United States Patent [19]

Holtkamp

[11] Plant 4,303

[45] Sep. 19, 1978

[54] AFRICAN VIOLET PLANT

[75] Inventor: Reinhold Holtkamp, Isselburg, Fed. Rep. of Germany

[73] Assignee: Gesellschaftsvertrag uber die Erfindergemeinschaft "Optimara", Isselburg, Fed. Rep. of Germany

[21] Appl. No.: 786,853

[22] Filed: Apr. 12, 1977

[51] Int. Cl.[2] ..... A01H 5/00

[52] U.S. Cl. ..... Plt./69

[58] Field of Search ..... Plt./69

*Primary Examiner*—Robert E. Bagwill
*Attorney, Agent, or Firm*—Donald D. Jeffery

[57] ABSTRACT

An African violet cultivar having vigorous growth and generally purple flowers and medium green leaves. The cultivar has 10–15 upright and strong flower stems, with each stem carrying up to 10 flowers, thereby providing a very strong and full flowerhead.

1 Drawing Figure

The present invention comprises a new and distinct cultivar of African violet plant, botanically known as *Saintpaulia ionantha,* and hereinafter referred to by the cultivar name California.

The new cultivar, designated during the breeding and selection process by the designation b. 226/2 - 5/76, is a product of a planned breeding program. The seed parent is a blue semidouble violet identified as type 26/74, and the pollen parent, identified as type XIX 4158, is a bordeaux red single variety. California has certain desired characteristics from both parents, for example, the new variety has up to 15 flower stems with 5–10 flowers on each stem, a few of which are semidouble.

The new cultivar was originated from a cross made in Isselburg, Rhineland, Germany. The new cultivar was discovered and selected as a flowering plant within the progeny of the stated cross by me in a controlled environment in Isselburg, Rhineland, Germany.

Asexual reproduction of the new cultivar by leaf cuttings and by division of shoots, as performed by me at Isselburg, Rhineland, Germany, has demonstrated that the combination of characteristics as herein disclosed for the new cultivar are firmly fixed and are retained through successive generations of asexual reproduction.

The following observations, measurements and values describe plants grown in Isselburg, Rhineland, Germany, under greenhouse conditions which closely approximate those generally used in commercial practice.

The following traits have been repeatedly observed and are determined to be basic characteristics of California which in combination distinguish this African violet as a new and distinct cultivar:

1. 10–15 flower stems with up to 10 flowers on each stem, with the flowers being generally purple in color.
2. Upright, strong flower stems.
3. Vigorous growth.
4. Strong upright peduncle.
5. Long blooming period.
6. Attractive saleable plant with the first flash of flowers.
7. Medium green colored foliage.

The accompanying photographic drawing shows a typical specimen plant of the new cultivar. The colors appearing in the photograph are as true as possible with color illustrations of this type. In the following description, color references are made to The Munsell Limit Color Cascade, 1972 edition, except for the individual flower color values, which are based on R.H.S. Colour Chart, 1966 edition. It should be noted that the flower color values were taken in early April in natural light from a plant in full bloom, with the flowers being slightly faded. In addition, the color of the leaves in the photograph is slightly darker than the true color of the leaves.

Botanical classification: *Saintpaulia ionantha,* Ramat. cv. California.

Parentage:

*Male parent.*—XIX 4158 bordeaux red, color 44–44.

*Female parent.*—26/74 blue, color 1-12.

Plant: From 7 cm. to 9 cm. tall when grown in pots, and approximately 25 cm. in diameter when fully grown.

*Leaves.*—General form: Oval to heart-shaped. Diameter: 55-60 when fully developed. Texture: Soft, slightly hairy. Aspect: Velvety. Veins: Underside well pronounced, light green. Color (upperside): Color 21-14. Color (underside): Light green, shiny. Petiole: On young leaves, brown-reddish; on older leaves turning more to light reddish.

*Flowers.*—Buds: Ballshaped, 8 mm. in diameter before opening; outside color, violet-blue. Sepals: Color: 26 - 13. Calyx: Funnel-shaped. Aspect: Spear-shaped, 5 mm long. Peduncle: Reddish from stem to calyx.

*Individual flowers.*—Size: 40–45 mm. in diameter; funnel-shaped after opening; when fully mature, almost flat. Color: Upperside: 83 B-C, fading to approximately 82A; underside: 82 B-C. Borne: Normally 7–10 flowers on strong stems and peduncles. Shape: Five petals, 2 small and 3 large; most flowers are single, a few tend to semidouble. Corolla: The petals are uniform in color, but the center of the flower changes to velvety dark violet, 48-10, when the plant is in full flower approximately after 4–6 weeks. Arrangement: Very rich flowerhead when plant is at maturity. Flowering time: Approximately 6–8 weeks after potting, the plant is saleable with the first flowers, and there are many buds below the open flowers.

*Reproductive organs.*—Anthers: Two to four cells, golden yellow 25-5. Arrangement: Basifixed. Filaments: Light green on one side, violet stripe from base to the cells. Styles: 7 mm. long, color 47-14; base is very hairy, color 20-1. Pollen color: 26-1. Roots: The cultivar has a well-developed root system. Disease resistance: Excellent resistance to mildew and botrytis, as experienced to date.

*General observations.*—California is a vigorous grower and highly attractive with its medium green leaves and generally purple flowers. When the plant shows the buds and the first flowers, there is a great abundance of flower stems. When the plant is in full flowering, the flowerhead is strong and robust due to the numerous strong flower stems. The flowers do not drop after withering thereby avoiding damage due to botrytis from fallen blossoms.

I claim:

1. A new and distinct cultivar of African violet known by the cultivar name California and particularly characterized as to uniqueness by the combined characteristics of upright, strong flower stems each of which carries up to ten generally purple flowers; vigorous growth habit, upright, strong peduncle, medium green foliage, long blooming period, strong and robust flowerhead, and by its saleability after the first flash of flowers.

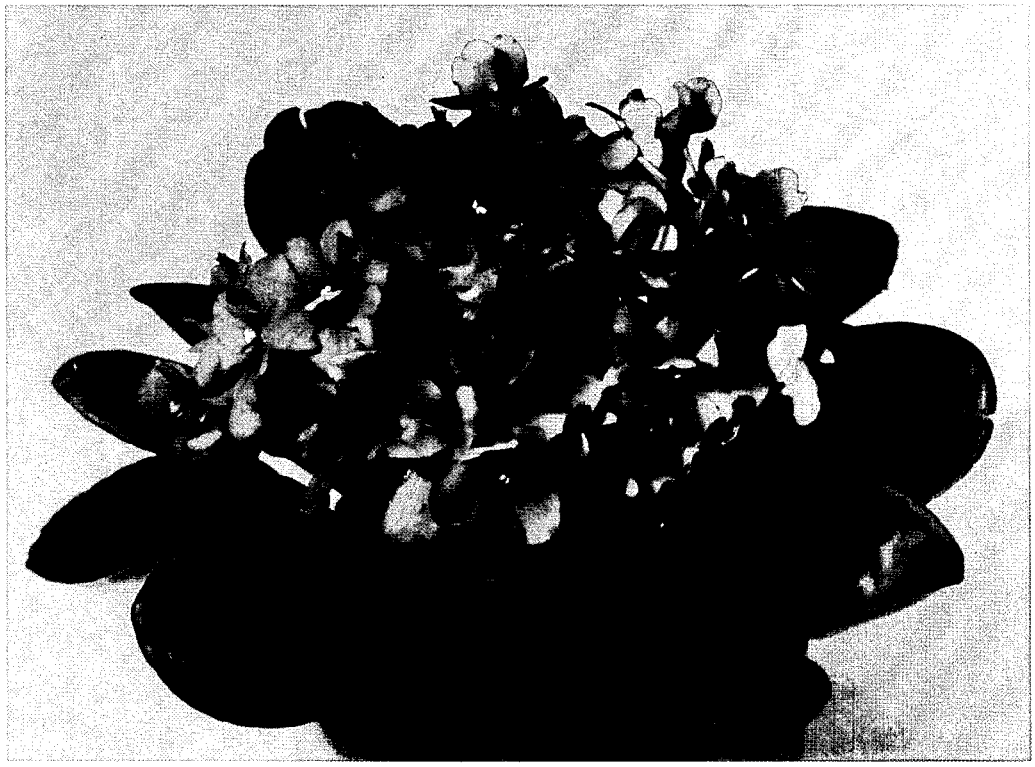

* * * * *